United States Patent [19]

Struckhoff et al.

[11] Patent Number: 6,020,969
[45] Date of Patent: Feb. 1, 2000

[54] CIGARETTE MAKING MACHINE INCLUDING BAND INSPECTION

[75] Inventors: Andrew D. Struckhoff, Alexandria; Lee C. Cramer, Springfield; Steven F. Spiers, Richmond; Gordon H. Bokelman, Chesterfield; Bogdan N. Alexander, Richmond; Mark Roth, Annandale, all of Va.

[73] Assignee: Philip Morris Incorporated, New York, N.Y.

[21] Appl. No.: 08/893,505

[22] Filed: Jul. 11, 1997

[51] Int. Cl.[7] .................................................. G01N 21/89
[52] U.S. Cl. ............................ 356/430; 348/88; 131/907
[58] Field of Search .................................. 356/429, 430, 356/431; 348/88; 131/907, 908

[56] References Cited

U.S. PATENT DOCUMENTS

| | | |
|---|---|---|
| 3,089,497 | 5/1963 | Molins et al. . |
| 3,588,513 | 6/1971 | Akamatsu et al. . |
| 3,818,223 | 6/1974 | Gibson et al. . |
| 3,955,584 | 5/1976 | Molins et al. . |
| 4,001,579 | 1/1977 | Lebet et al. . |
| 4,011,950 | 3/1977 | McLoughlin et al. . |
| 4,054,377 | 10/1977 | Gibson . |
| 4,090,794 | 5/1978 | Benini . |
| 4,099,884 | 7/1978 | Nash . |
| 4,212,541 | 7/1980 | Ducommun et al. . |
| 4,238,994 | 12/1980 | Koch . |
| 4,266,674 | 5/1981 | Bell et al. . |
| 4,377,743 | 3/1983 | Bolt et al. . |
| 4,398,546 | 8/1983 | Fisher et al. . |
| 4,423,742 | 1/1984 | Reuland . |
| 4,645,921 | 2/1987 | Heitmann et al. . |
| 4,671,663 | 6/1987 | Sick . |
| 4,682,038 | 7/1987 | Focke . |
| 4,718,026 | 1/1988 | Long et al. . |
| 4,756,317 | 7/1988 | Edwards . |
| 4,766,315 | 8/1988 | Hellstrom et al. . |
| 4,767,924 | 8/1988 | Giebel et al. . |
| 4,776,351 | 10/1988 | Wahle et al. . |

(List continued on next page.)

OTHER PUBLICATIONS

"More Feedback: Process Control Leaps Ahead With New ABB Solutions [For Tobacco Manufacturing]", Tobacco Reporter (Nov./1994) vol. 121, No. 11, p. 26, Doolittle, David E.

*Primary Examiner*—Richard A. Rosenberger
*Attorney, Agent, or Firm*—Burns, Doane, Swecker & Mathis, L.L.P.

[57] ABSTRACT

An optical inspection system mounts on a cigarette making machine or like system and detects the presence of bands having irregular widths or spacings. In response to the detection of irregular bands, the optical inspection system instructs the cigarette making machine to reject cigarettes which will be subsequently made from portions of the cigarette paper containing the irregular bands. The optical inspection system includes a sensor which can accommodate different types of cigarette paper and band material having varying reflectance properties. In operation, sensor circuitry detects the range of voltages produced by a sensor detector, and formulates a peak value (or average peak value) for the range of voltages. The circuitry then takes a percentage of this peak value to form a threshold value. This threshold value is compared with the AC signal from the sensor detector. If the AC signal exceeds the threshold, then the circuitry asserts a signal to indicate that a band is present. The output of the sensor is fed to a computer. The computer detects whether the bands detected by the sensor have regular band spacing and width.

14 Claims, 13 Drawing Sheets

U.S. PATENT DOCUMENTS

| | | |
|---|---|---|
| 4,805,641 | 2/1989 | Radzio et al. . |
| 4,841,763 | 6/1989 | Kang et al. . |
| 4,845,374 | 7/1989 | White et al. . |
| 4,860,772 | 8/1989 | Hensgen et al. . |
| 4,865,054 | 9/1989 | Lorenzen et al. . |
| 4,875,494 | 10/1989 | Siems . |
| 4,879,000 | 11/1989 | Gausa . |
| 4,906,099 | 3/1990 | Casasent . |
| 4,907,607 | 3/1990 | Focke et al. . |
| 4,915,827 | 4/1990 | Rosenthal . |
| 4,926,886 | 5/1990 | Lorenzen et al. . |
| 4,941,482 | 7/1990 | Heitmann et al. . |
| 4,963,743 | 10/1990 | Satake et al. . |
| 4,976,544 | 12/1990 | Neri . |
| 4,982,104 | 1/1991 | Yuito . |
| 4,986,285 | 1/1991 | Radzio et al. . |
| 5,000,323 | 3/1991 | Cahill et al. . |
| 5,006,722 | 4/1991 | Adelson . |
| 5,010,904 | 4/1991 | Lassiter . |
| 5,013,905 | 5/1991 | Neri . |
| 5,024,333 | 6/1991 | Brink et al. . |
| 5,061,063 | 10/1991 | Casasent . |
| 5,072,128 | 12/1991 | Hayano et al. . |
| 5,086,279 | 2/1992 | Wochnowski et al. . |
| 5,118,195 | 6/1992 | Dobbie . |
| 5,150,175 | 9/1992 | Whitman et al. ................... 356/429 |
| 5,166,748 | 11/1992 | Dahlquist . |
| 5,189,708 | 2/1993 | Cox et al. . |
| 5,208,870 | 5/1993 | Ennis . |
| 5,223,915 | 6/1993 | Neri . |
| 5,228,462 | 7/1993 | Osmalov et al. . |
| 5,235,649 | 8/1993 | Reda . |
| 5,237,621 | 8/1993 | Cox et al. . |
| 5,243,408 | 9/1993 | Whitman, III . |
| 5,305,392 | 4/1994 | Longest, Jr. et al. . |
| 5,341,824 | 8/1994 | Fletcher et al. . |
| 5,345,955 | 9/1994 | Clearman et al. . |
| 5,353,357 | 10/1994 | Longest, Jr. et al. . |
| 5,365,596 | 11/1994 | Dante et al. . |
| 5,366,096 | 11/1994 | Miller . |
| 5,406,376 | 4/1995 | Maiwaid et al. . |
| 5,410,396 | 4/1995 | Rochester . |
| 5,414,270 | 5/1995 | Henderson et al. . |
| 5,426,509 | 6/1995 | Peplinski . |
| 5,432,600 | 7/1995 | Grollimund et al. . |
| 5,448,365 | 9/1995 | Grollimund et al. . |
| 5,534,114 | 7/1996 | Cutright et al. . |
| 5,641,971 | 6/1997 | Prigent . |
| 5,718,249 | 2/1998 | Suzuki et al. . |
| 5,746,225 | 5/1998 | Okumoto et al. . |
| 5,762,075 | 6/1998 | Hoppe et al. . |

SETUP INFORMATION

| | |
|---|---|
| Minimum Band Width (mm): | 4.25 |
| Maximum Band Width (mm): | 6.00 |
| Minimum Band Spacing (mm): | 15.50 |
| Maximum Band Spacing (mm): | 25.75 |

BAND INFORMATION

| | |
|---|---|
| Bands Within Limits: | 234598 |
| Bands Outside Limits: | 10 |
| Spaces Outside Limits: | 0 |

MEASUREMENTS

| | Avg | Std |
|---|---|---|
| Width (mm): | 5.22 | 0.1 |
| Spacing (mm): | 19.79 | 0.3 |

MESSAGES & INSTRUCTIONS

Press 'g' to inspect or 's' to stop

INSPECTION STATUS

| | |
|---|---|
| Inspecting: | YES |
| Sensor Alarm: | No |

ENCODER INFORMATION

| | | Min | Max |
|---|---|---|---|
| Paper Speed (mm/s): | 4056.3 | 4.50 | 6.25 |
| | | 19.50 | 22.75 |

FIG. 12

CIGARETTE MAKING MACHINE INCLUDING BAND INSPECTION

CROSS REFERENCE TO RELATED APPLICATIONS

The present application is related to commonly assigned Ser. No. 08/893,500 entitled "Bobbin Optical Inspection System", which was filed on the same date as the present application and is hereby incorporated by reference in its entirety.

BACKGROUND

The present invention relates to a cigarette making machine including a system and method for assuring that bands formed on cigarette paper have proper width and spacing, and for rejecting cigarettes made from cigarette paper having out-of-tolerance band widths and spacings.

To ensure a high quality product, many manufacturers install optical inspection systems at various stages in the production line of an article of manufacture. Typically, each inspection station will include a source of electromagnetic radiation which directs the radiation toward the surface of the article of manufacture where it creates reflections. One or more sensors receive the reflections. Analysis of the received reflections provides insight into the characteristics of the article of manufacture, and in particular, whether the article may be irregular.

Prior art sensors of the type described above are typically designed and calibrated to detect specific articles. As such, these sensors can not easily be adapted to perform similar analysis on different articles. If the article changes, the manufacturer will be forced to redesign the sensor for compatibility with the new article. For instance, an engineer or technician might have to replace one or more circuit components associated with the sensor to calibrate the gain of the sensor's circuitry to accommodate different articles with varying reflectance properties.

Moreover, prior art optical inspection systems are primarily directed to ascertaining the presence of localized point anomalies, such as pinholes, tears and blemishes in a web of material. U.S. Pat. No. 5,426,509 to Peplinkski exemplifies this technique. In this system, the presence of an anomaly in a moving web causes a "spike" in the output of a sensor, which may be visualized using an oscilloscope. However, other anomalies are characterized by irregularities in the spatial relationship between elements or portions of the article of manufacture. An isolated analysis of a single point on an article, as described above, will not reveal these anomalies.

By way of illustration, consider the manufacture of banded cigarettes, one of which is illustrated in FIG. 1. As shown there, the cigarette 7 contains two bands 5 of material formed by depositing a layer of cellulosic pulp on base cigarette paper 3. Cellulon, microcrystalline cellulose, or amylopectin are various substances which have been used to form the bands. In order to provide a high quality product, it is desirable to ensure that the paper used to manufacture these cigarettes contains bands 5 having the proper width. Moreover, it is necessary to ensure that the spacing between adjacent bands is within tolerance. As illustrated in FIG. 2, cigarette paper 3 contains bands having proper widths (e.g. bands $B_1-B_5$), and at least one band having an out-of-tolerance width (e.g. band $B_6$). Also, the cigarette paper contains at least two adjacent bands having a spacing which is out-of-tolerance (e.g. the spacing between bands $B_4$ and $B_5$). The above described prior art optical inspection systems do not have the capability of detecting these anomalies.

Accordingly, it is an objective of the present invention to provide a system and method for analysis of a web of material, which does not suffer from the above noted drawbacks. It is another exemplary objective of the present invention to provide a sensor which can detect anomalies on different types of web materials without requiring a burdensome redesign or recalibration of the sensor. It is another exemplary objective of the present invention to provide an optical inspection system which ascertains whether paper containing bands includes bands having out-of-tolerance band widths, or out-of-tolerance spacings between adjacent bands.

It is a more specific objective of the present invention to provide a system and method for inspecting cigarette paper containing bands in a cigarette making machine and for rejecting cigarettes made from irregular sections of the cigarette paper.

SUMMARY

These and other exemplary objectives are achieved according to the present invention through an optical inspection system which mounts on a cigarette making machine or like system and detects the presence of bands having irregular widths or spacings therebetween. Cigarettes constructed with irregular portions of the cigarette paper are tracked as they progress through the cigarette making machine and are ejected at one of the rejection ports of the cigarette making machine.

The optical inspection system includes a sensor which can accommodate different types of cigarette paper and band material having varying reflectance properties. In operation, sensor circuitry detects the range of voltages produced by a sensor detector, and formulates a peak value (or average peak value) for the range of values. The circuitry then takes a prescribed percentage of this peak value to form a threshold value. This threshold value is compared with an AC signal from the sensor detector. If the AC signal exceeds the threshold, then the circuitry asserts a signal to indicate that a band is present.

The circuitry includes an AC amplifier for amplifying AC components of signals from the sensor detector. To further accommodate different types of paper and band material having varying reflectance properties, the gain of this amplifier can be adjusted, such as by adjusting the setting of a dip switch. Similarly, the threshold value selected by the threshold circuitry can be adjusted to chose one of a plurality of different threshold values (e.g. 30%, 40%, 50%, 60%, etc.).

BRIEF DESCRIPTION OF THE DRAWINGS

The foregoing, and other, objects, features and advantages of the present invention will be more readily understood upon reading the following detailed description in conjunction with the drawings in which:

FIG. 12 shows an exemplary display for presenting statistics regarding the integrity of band widths and spacings analyzed by the sensor and associated computer according to the present invention.

DETAILED DESCRIPTION

In the following description, for purposes of explanation and not limitation, specific details are set forth in order to provide a thorough understanding of the invention. However it will be apparent to one skilled in the art that the present invention can be practiced in other embodiments that depart from these specific details. In other instances, detailed descriptions of well-known methods, devices, and circuits are omitted so as not to obscure the description of the present invention with unnecessary detail. In the Figures, like reference numbers designate like parts.

Figure 3:
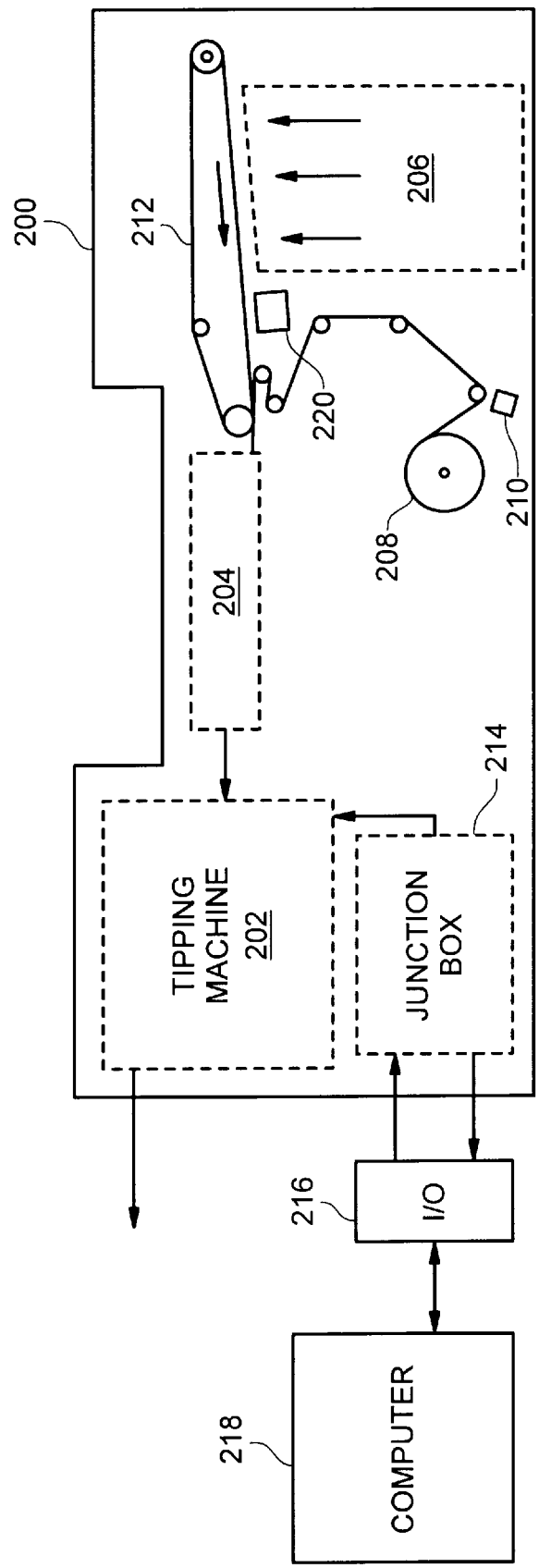
FIG. 3 shows an exemplary cigarette making machine including a sensor (210) for detecting bands.

FIG. 3 shows an overview of a cigarette making machine 200 including a sensor 210 for detecting bands formed on cigarette paper fed from bobbin 208. As is well known in the art, air flows through a passage 206 and blows tobacco particles upward onto a conveyer belt 212. The particles adhere to the conveyer belt 212 in response to a suction force applied through perforations in the conveyer belt 212. The particles form a layer of tobacco on the underside of the conveyer belt 212 as the conveyer belt 212 moves from right to left. At a certain point in the conveyer belt's path, a trimmer 220 removes excess tobacco from the layer (forming a cigarette filler rod) by means of rotating disks or the like.

Figure 1:
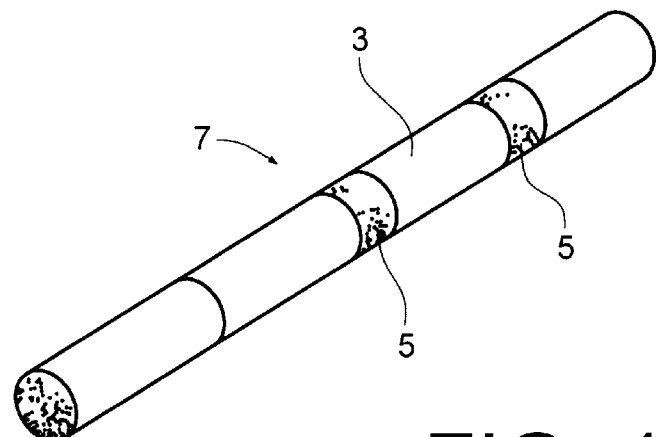
FIG. 1 shows an exemplary cigarette containing banded regions.
Figure 2:
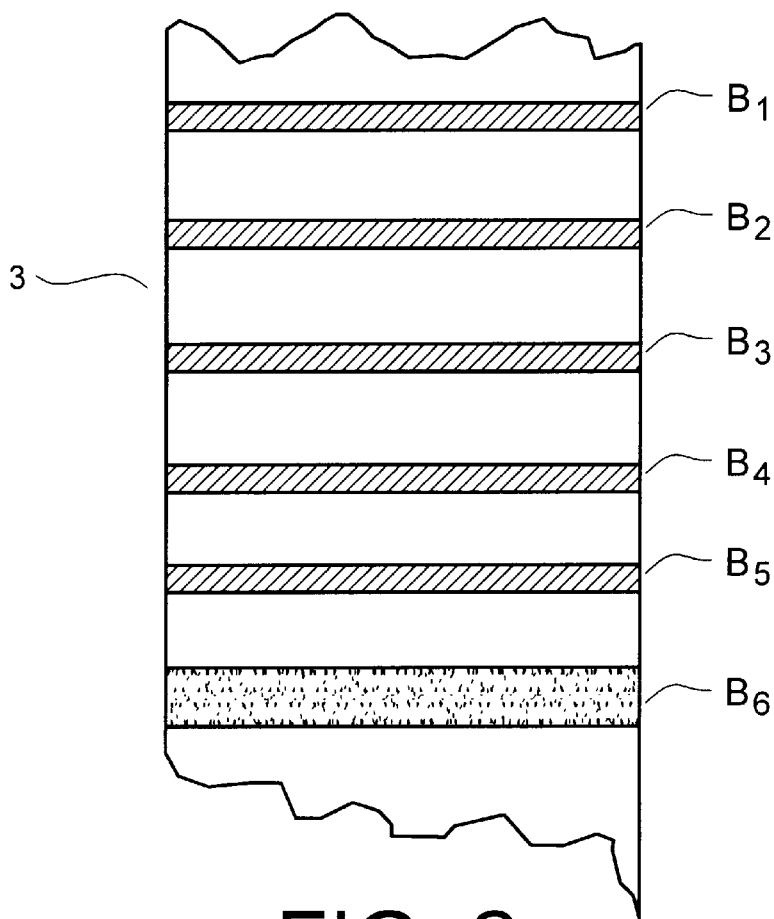
FIG. 2 shows an exemplary web of cigarette material including bands, some of which are irregular.

Simultaneously with the formation of the filler rod on the conveyer belt 212, cigarette paper containing bands (e.g. a section of which is shown in FIG. 2) is fed from a feeder bobbin 208 to a region underneath one end of the conveyer belt 212. At that point, the conveyer belt 212 transfers the tobacco held on the belt to the cigarette paper. The cigarette paper is then wrapped around the filler rod and glue is applied to the assembly to secure the cigarette paper to the filler rod. The rod is then cut into individual tobacco rods (e.g. such as double length tobacco rods from which two cigarettes will be manufactured). The above-referenced wrapping, gluing and cutting are conventional in the art and thus are represented as simply rod forming unit 204 in FIG. 3 so as not to obfuscate FIG. 3.

Figure 4:
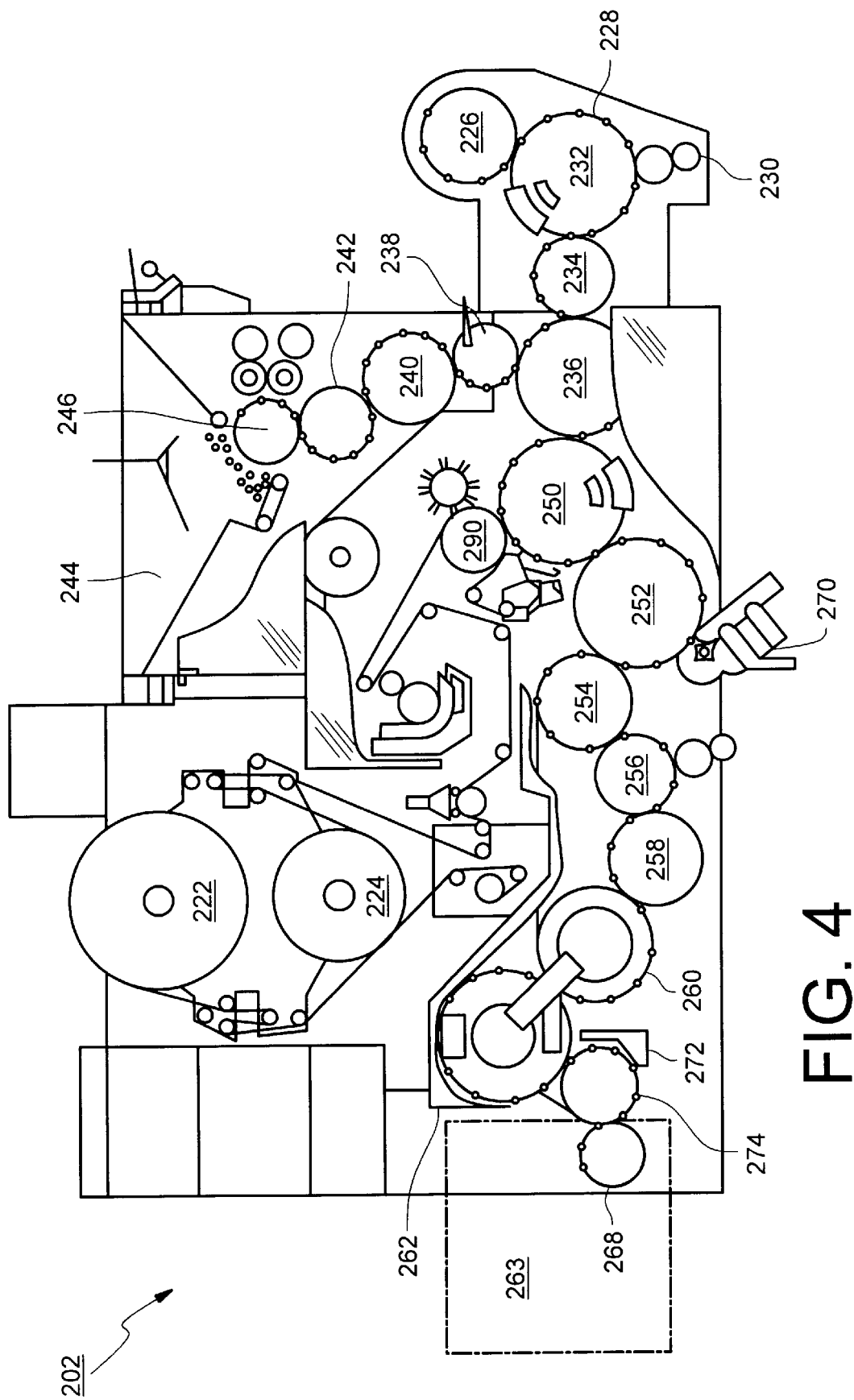
FIG. 4 shows an exemplary tipping machine for use in the machine of FIG. 3.

After the tobacco rods (e.g. double length tobacco rods) have been formed in this manner, they are transferred to a tipping machine 202 which adds filter rods to the tobacco rods to form a plurality of finished cigarettes. The tipping machine can comprise the conventional MAX 100 machine produced by Hauni-Werke Körber and Co., AG, Hamburg, Germany. This machine is illustrated in FIG. 4. As shown there, the machine includes a rotary drum 226 which transfers double length rods formed by rod forming unit 204 to rotary drum 232, which cuts the double length rods in half to form single length tobacco rods using rotary cutter 230. The Drum 234 separates the two single length tobacco rods so that a filter plug can be inserted between the tobacco rods.

The filter rods originate from bin 244, where they are originally in 4-up form (that is, comprising a length corresponding to four filter plugs). The filter rods are transferred to drum 236 via drums 246, 242, 240 and 238. Drum 246 additionally cuts the 4-up filter plugs into two 2-up filter plugs. At drum 236, the filter plugs are inserted between the separated tobacco rods from drum 234. The filter plugs and the tobacco rods are then transferred to drum 250 which applies tipping paper from bobbins 222 or 224 to the combination of tobacco rods and filter plugs by drum 290. The tipping paper is wound around the combination of the tobacco rods and filter plugs at drum 252 using wrapping device 270. The resultant cigarette rods are then transferred to drum 254 and then to drum 256. At drum 256 the cigarette rods are cut in half to form individual cigarettes. The cigarettes are then transferred via drums 258, 260, 262, 274 and 268 to output bin 263. Irregular cigarettes, however, are ejected at output drum 274 without entering the output bin 263. There are other rejection ports in the tipping machine discussed above, such as at drums 252, 256, and 236. Also, although not illustrated in detail, various rejection ports exist further upstream in the tobacco rod making portion of the machine, as will be understood by those skilled in the art.

Returning to FIG. 3, the sensor 210 can be located adjacent to an idler roller or guidepost over which the banded cigarette paper passes. However, this location is entirely exemplary. The sensor 210 can be located at other locations. Furthermore plural sensors can be located at various locations in the cigarette making machine.

As will be discussed in greater detail later, the sensor 210 generates an output signal indicative of bands sensed on the passing cigarette paper. According to one embodiment, the output of the sensor is a pulse train, where the duration of each pulse corresponds to the duration of each respective sensed band. The pulse train output of the sensor is then directed to an external I/O interface 216. The output of the sensor can be directly fed to the interface 216, or can be sent to the cigarette making machine's junction box 214, and then transferred to the interface 216. The I/O interface 216 also receives data from the cigarette making machine's encoder (not shown), which indicates the rate at which the machine is operating (e.g. the rate of transfer of tobacco rods through the system), as measured, for example, by the rate of rotation of one of the mechanical shafts in the machine. The sensor output and the encoder output are then transferred to external computer 218 which includes an associated counter/timer board and an I/O board (not shown). More specifically, the computer is a separate workstation, and can comprise a Pentium 133 MHz microprocessor, a monitor, keyboard, hard drive and floppy disk drive (not shown). A Computer Boards™ CIO-DIO24H can be used for the I/O board, while a Computer Boards™ CIO-CTR05 can be used for the counter board. The computer 218 determines whether the sensed band widths and band spacings are out-of-tolerance based on the sensor's output and based on the encoder's output.

If the band widths and/or band spacings are out-of-tolerance, the computer provides a signal to the cigarette making machine 200 via the junction box 214 to reject cigarettes which are made from the irregular portions of the cigarette paper. More specifically, the location of irregular cigarette paper after it passes the sensor 210 can be tracked using timing pulses generated by the machine's encoder.

That is, by counting the timing pulses the system can predict when a cigarette will pass one or more rejection ports (such as rejection ports corresponding to drums 274, 252, 256 and 236 in FIG. 4, as well as other rejections ports not specifically illustrated). When the irregular cigarette passes a rejection port (as indicated by the counter reaching a prescribed count), it is ejected by the cigarette making machine. Those skilled in the art will appreciate that there are other ways to control the rejection of cigarettes. For instance, another way of performing this function is to set a timer with an initial value corresponding to the time it takes (depending on the speed of the machine) for an irregular section of the paper to pass a rejection port. When the timer counts down, the cigarette containing that irregular section is located at the rejection port and is therefore ejected. In general terms, the proper timing for the rejection of cigarettes can be determined from knowledge of the characteristics of the cigarette transfer path (such as the distance between the sensor and various downstream locations in the path) and the speed at which the machine is operating.

The function of the sensor and the computer can be better understood with reference to the following discussion and accompanying drawings. The mechanical and electrical components of the sensor are discussed first, followed by a discussion of the analysis performed by the computer.

Figure 5:
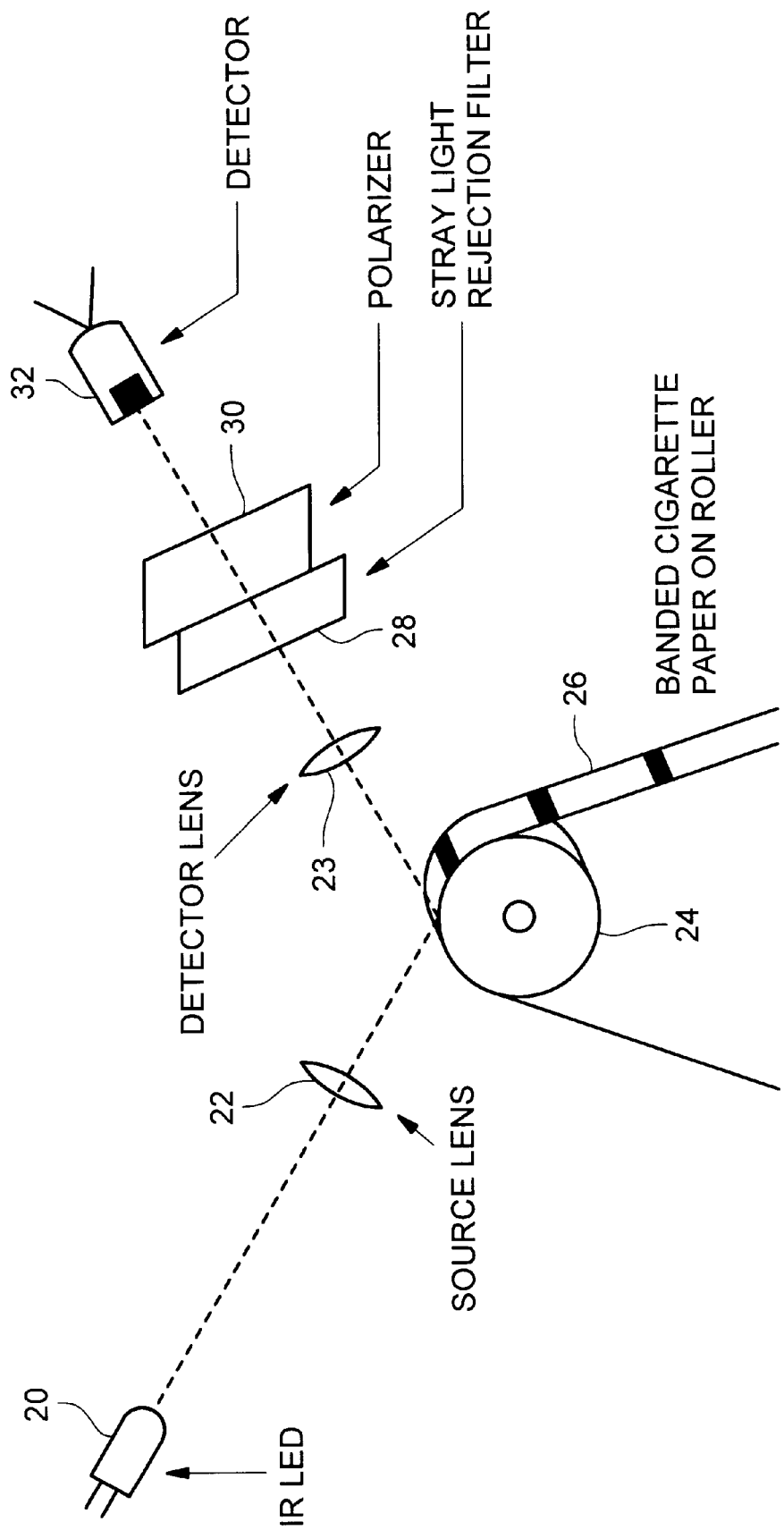
FIG. 5 shows exemplary optical components of the sensor according to the present invention.

Starting with FIG. 5, the sensor includes an infrared LED 20 for emitting infrared radiation. For example, the LED 20 can be chosen to emit radiation having a wavelength of 850 nm, (+ or −20 nm). The infrared radiation from the LED 20 is focused by source lens 22 to form a 1 mm diameter spot on banded paper 26 as the paper 26 passes over a roller 24.

The infrared light which impinges on the surface of the paper 26 as it passes over the roller 24 creates reflections. These reflections are passed through a detector lens 23 which focuses the reflected light on a stray light rejection filter 28 and then a polarizer 30. The stray light rejection filter 28 filters out the majority of ambient light (occurring at frequencies which differ from the infrared radiation produced by LED 20). The polarizer 30 chooses light having a prescribed linear polarization direction which accentuates the difference in reflections from the banded regions on the paper 26 and the base paper. The stray light rejection filter 28 and the polarizer 30 can optionally be omitted if the paper exhibits reflectance properties which distinctly separate band portions from non-band portions (i.e. the signal-to-noise ratio is large enough). Finally, the reflected light is received by a photodetector 32 which converts the reflected infrared radiation to an electrical signal proportional to the magnitude of radiation sensed.

Figure 6:
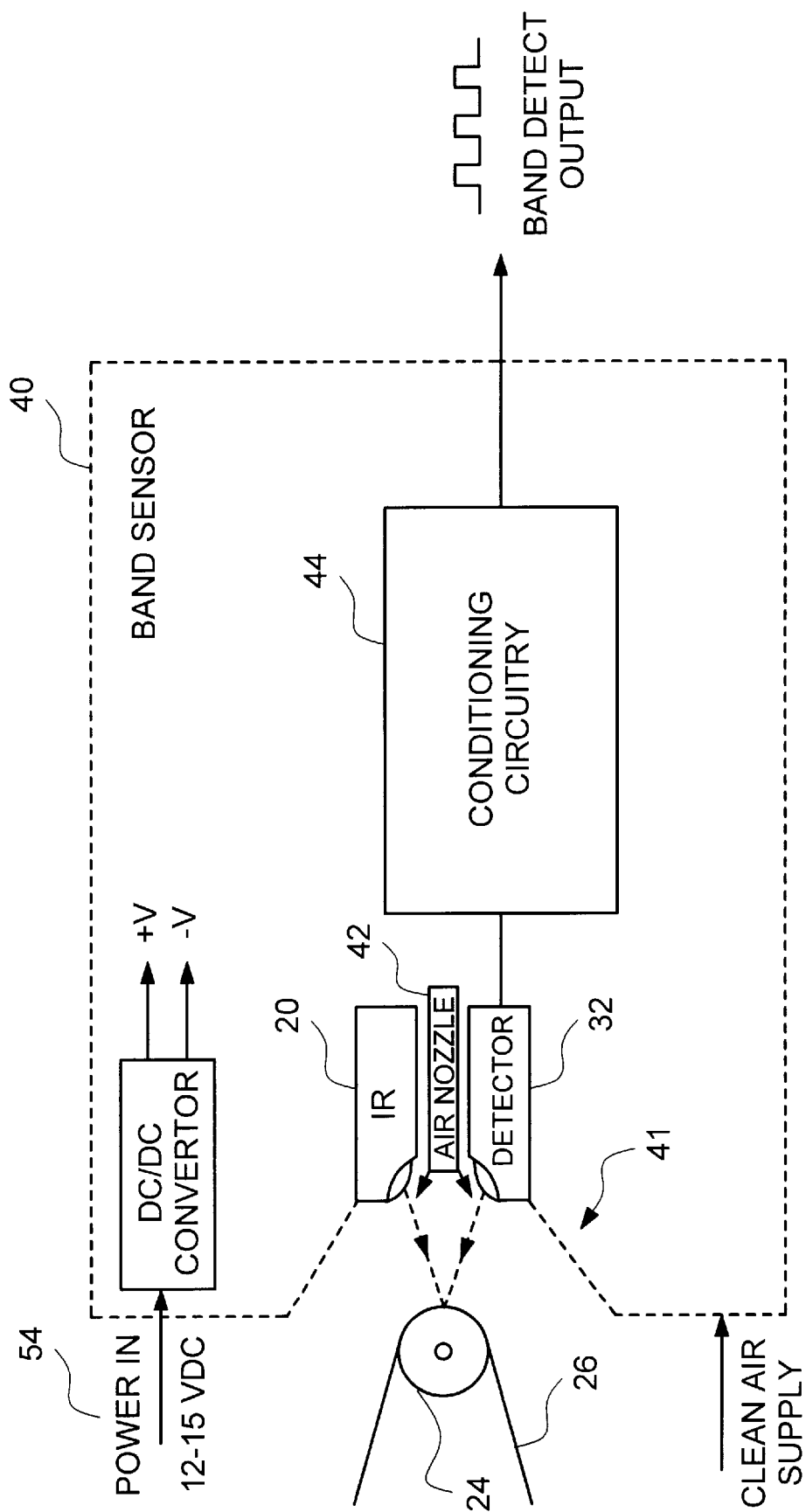
FIG. 6 shows an exemplary overview of the sensor according to the present invention.

The above described components are housed within an enclosure 40, as illustrated with reference to FIG. 6. As shown there, the enclosure 40 is generally rectangular in shape. The enclosure 40 includes a notch 41 which straddles the roller 24, a short distance above the roller 24. The infrared LED 20 is attached to one side of the notch 41, while the detector 32 is attached on the other side of the notch 41.

To keep dust and other residue from settling on the optical components, the sensor enclosure 40 includes a conduit 52 for receiving clean air. This clean air is directed to the optical components by means of air nozzle 42. Furthermore, the enclosure includes an input jack 54 for receiving electrical power to supply the conditioning circuitry 44 of the sensor with power.

Figure 7:
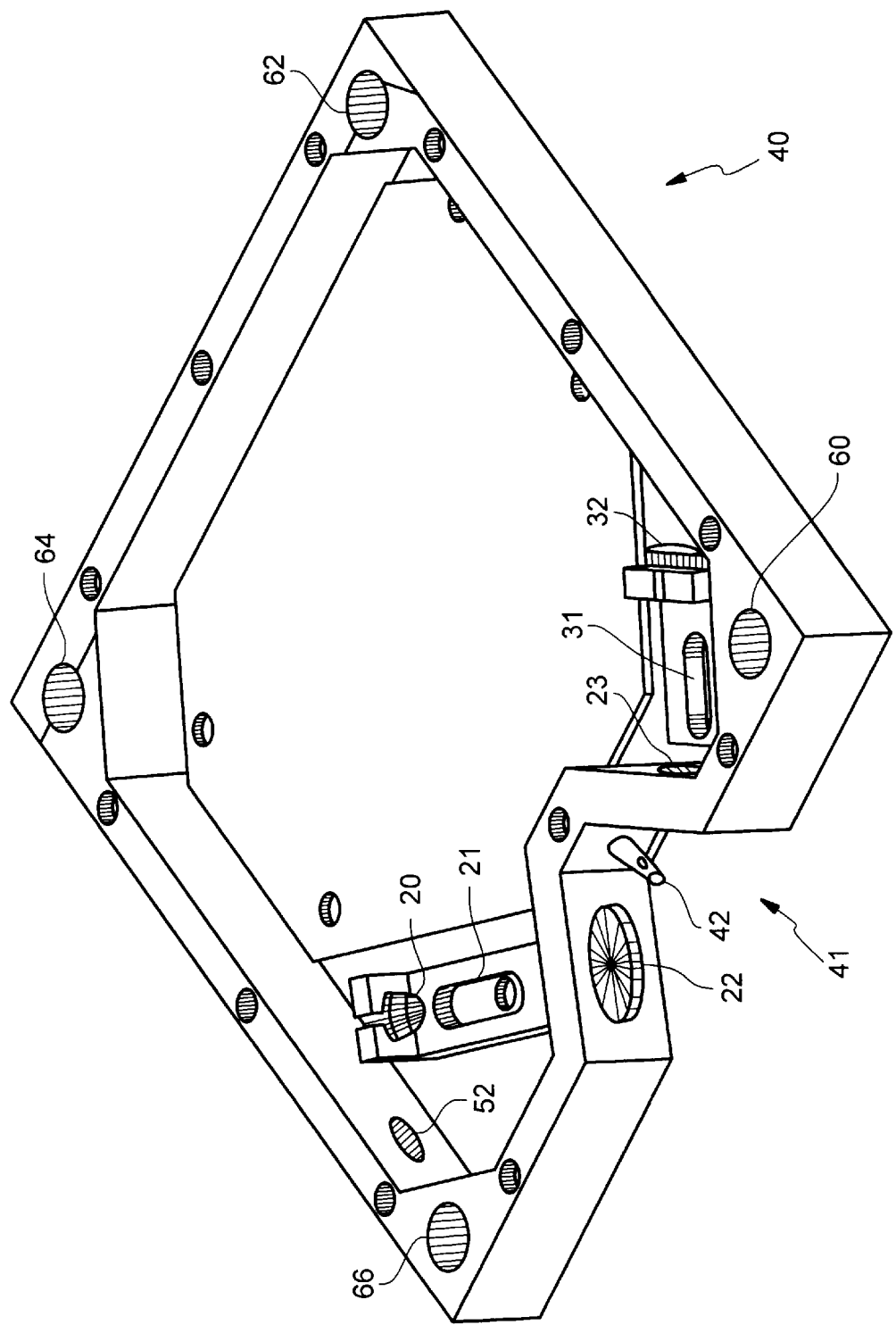
FIG. 7 shows an exemplary mechanical construction of the sensor housing according to the present invention.

A still more detailed exemplary illustration of the mechanical structure of the enclosure 40 can be found with reference to FIG. 7. As shown there, the enclosure includes a source lens 22 and detector lens 23 embedded in the sides of the notch 41. The infrared LED 20 is fixed in place in relation to the source lens 22 by means of a first frame 21. Similarly, the photodetector 32 is fixed in place with respect to the detector lens 23 by means of a second frame 31. Although not shown, the stray light rejection filter 28 and the polarizer 30 can also be accommodated within the second frame 31. Conduit 52 receives a supply of clean air, as discussed above, and channels the air to nozzle 42. The entire enclosure 40 can be fastened to its supporting structure by mean of bolt holes 60, 62, 64, and 66. The holes are oversized, so that the sensor can be first loosely attached to its supporting structure. Upon calibration and positional adjustments, the sensor can then be firmly bolted in place. Although not shown, the enclosure 40 includes a top plate which further protects the optical components from accumulating residue during operation which would degrade their performance.

Figure 8:
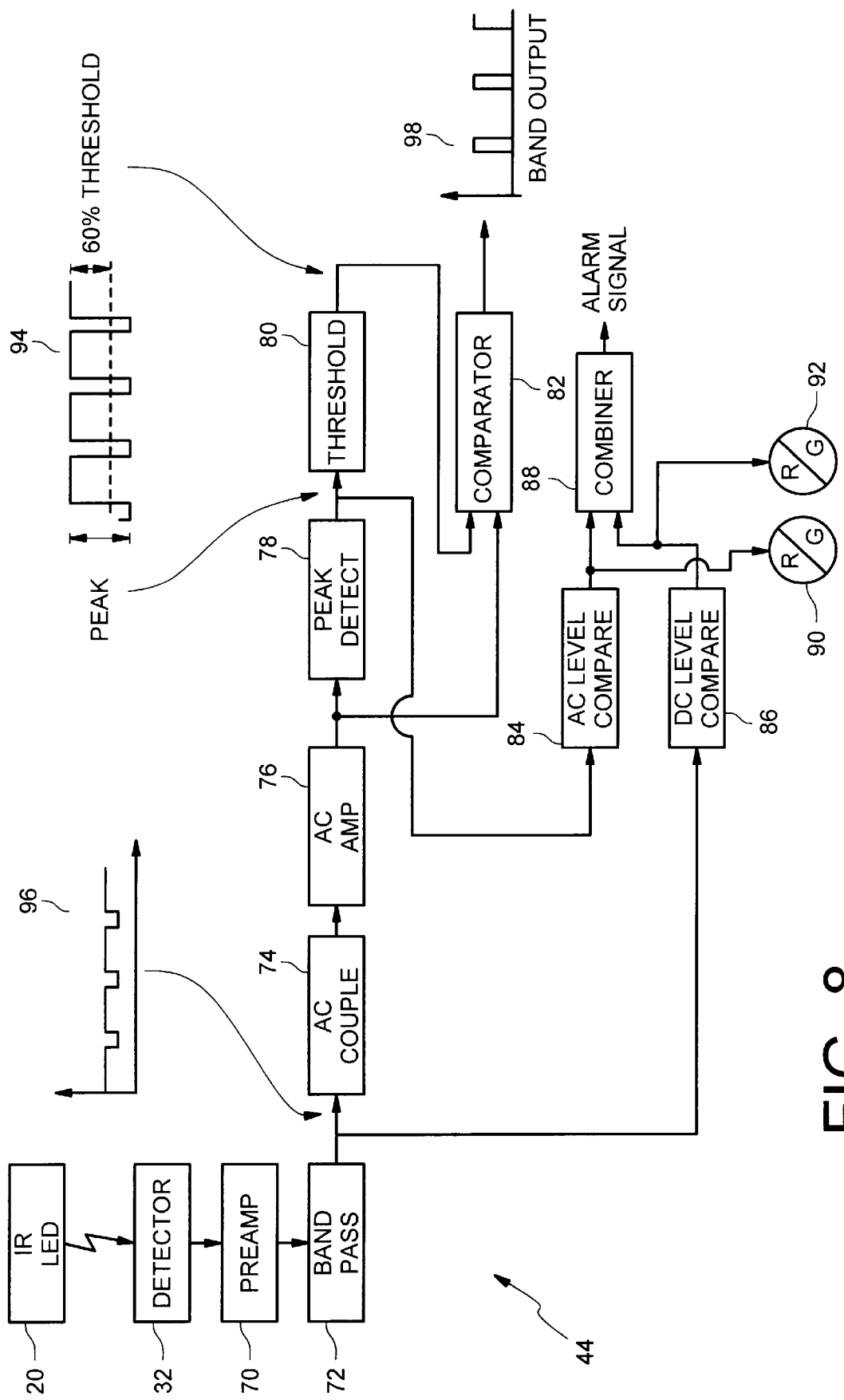
FIG. 8 shows exemplary electrical circuitry of the sensor used to detect the properties of banded paper according to the present invention.
Figure 9:
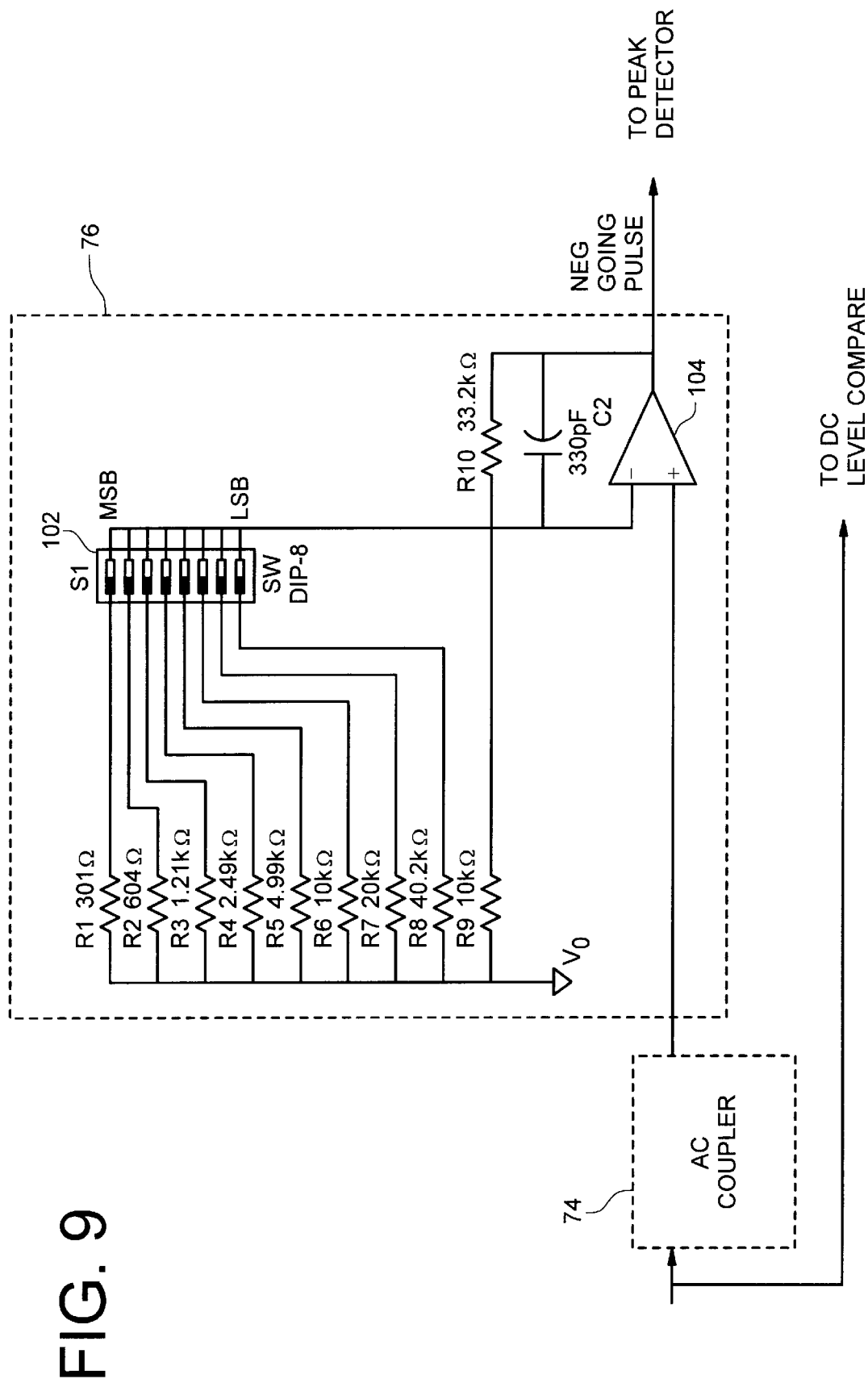
FIG. 9 shows a more detailed exemplary schematic of an AC amplifier used in the present invention.
Figure 10:
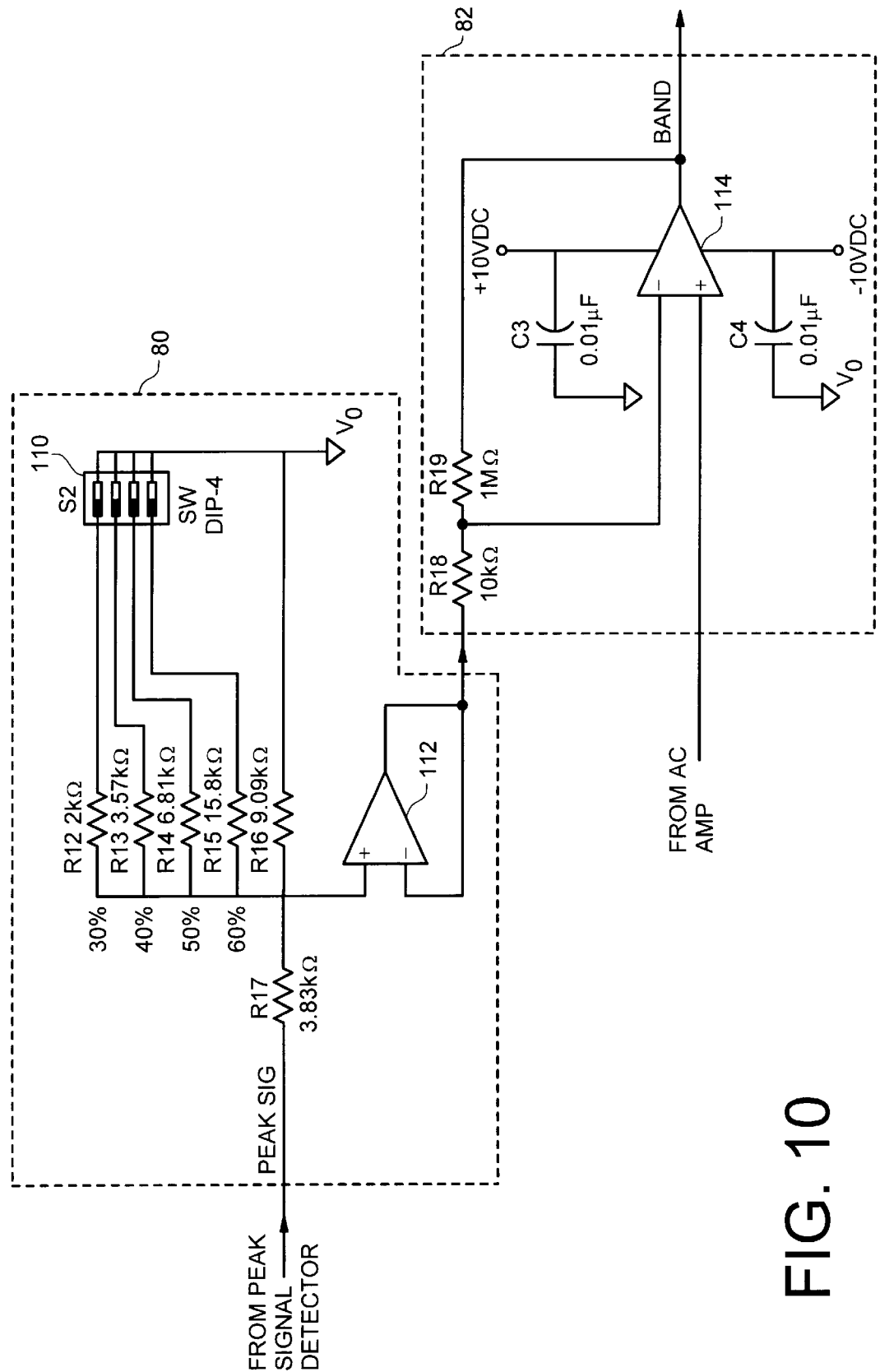
FIG. 10 shows a more detailed exemplary schematic of a threshold circuit and signal comparator used in the present invention.

The electrical configuration of the inspection system of the present invention can be understood with reference to FIGS. 8–10. FIG. 8 represents an overview of the circuitry 44 housed within the enclosure 40. As shown there, the detector 32 receives reflected infrared radiation from LED 20. The reflected radiation is converted into electrical signals and then amplified in preamp 70. The amplified signals are routed to bandpass filter 72 which removes extraneous signal response. At this point, as illustrated in waveform 96, the signal has both AC and DC components. The signal is a negative-going pulse, wherein a decrease in signal level is indicative of the presence of a band.

At this stage, the preamplified and bandpass filtered signal is routed to an AC coupler 74 which separates the AC from the DC component of the signal. The AC component is then fed to an AC amplifier 76. The AC amplifier 76 amplifies the AC component of the signal to a desired level. As will be described shortly with reference to FIG. 9, the gain of the AC amplifier 76 is adjustable to accommodate the use of the sensor with different types of webs having different reflectance characteristics. At this point, the signal resembles exemplary waveform 94.

Next, the amplified AC component is routed to a peak detector 78 which detects the magnitude of the peak voltage of the waveform (again, which can be appreciated with reference to waveform 94). According to one embodiment, the peak detector will form an average of the peak values of a plurality of successive waveform peaks. This value provides an indication of the general range of voltage between banded and non-banded regions on the paper, and can vary for different papers and different types of band material.

The average peak value is then transferred to a threshold circuit 80 which takes a certain percentage of the peak value for use as a threshold value. As shown with reference to the waveform 94, 60% of the peak waveform can be chosen as the value of the threshold. According to other embodiments of the invention, this threshold value is adjustable by the operator, and can assume any number of values (which will be discussed shortly in the context of FIG. 10).

The threshold value from the threshold circuit 80 is made available to the comparator circuit 82. The comparator circuit 82 compares the threshold with the AC component of the currently sensed signal. If the AC component is above the threshold, then the comparator circuit 82 generates a positive (or negative) pulse. In one embodiment, the comparator circuit may be set in a band-following mode. In this mode, the length of the pulse corresponds to the length of the detected band and the speed of the paper 26 moving over the roller 24. The output of this mode is illustrated by exemplary waveform 98.

In addition to the band detection output, the sensor also provides an alarm signal output. More specifically, the DC component of the signal is fed to a DC level comparator 86 which detects whether the DC level is either above or below a window of given voltage values. Similarly, the peak value of the AC component is transferred to an AC level comparator 84 which detects whether the AC level is either above or below a window of given voltage values. The output of each comparator is transferred to an LED (LEDs 90 and 92 respectively) which flashes red when the signal value is outside of the prescribed window, and flashes green when the signal value is within the prescribed window. The state of LEDs 90 and 92 thus provide useful diagnostic information regarding the status of the sensor. More particularly, the following table illustrates exemplary diagnostics for different states of LEDs 90 and 92.

| state | diagnostics |
| --- | --- |
| AC LED is green<br>DC LED is green | 1) The sensor is operating within tolerances. |
| AC LED is green<br>DC LED is red | 1) The sensor is misaligned; and/or<br>2) The reflective characteristics of the paper have changed; and/or<br>3) The sensor has malfunctioned. |
| AC LED is red<br>DC LED is green | 1) The paper is not moving; and/or<br>2) The sensor is misaligned; and/or<br>3) The reflective characteristics of the paper and/or band material has changed; and/or<br>4) The sensor has malfunctioned. |
| AC LED is red<br>DC LED is red | 1) There is no paper in the inspection area; and/or<br>2) The sensor is misaligned; and/or<br>3) The reflective characteristics of the paper has changed dramatically; and/or<br>4) The sensor has malfunctioned. |

The LEDs 90 and 92 can be physically affixed to the enclosure 40 of the sensor. Alternatively, if the sensor is positioned in a location which is not readily accessible, the LEDs 90 and 92 can be positioned remotely from the sensor enclosure 40.

In addition to the output of the LEDs 90 and 92, the conditioning circuitry 44 also transfers the alarm signals from comparators 84 and 86 to output combiner 88. This circuit generates a positive alarm signal when either comparator circuit 84 or 86 generates an alarm signal. Hence, the output combiner can use OR-gate circuitry or its equivalent, as will be readily understood by those skilled in the art. The output of the alarm combiner circuitry 88 and the comparator 82 are routed to an interface unit and then to a computer.

FIG. 9 illustrates an exemplary constitution of the AC amplifier 76 shown in FIG. 8. As shown there, the gain of the amplifier 104 with associated resistors R9 and R10 and capacitor C2, can be changed by the status of switches on DIP-switch 102. The DIP-switch, containing 8 switches, is connected to resistors R1–R8 having different values of resistance. According to exemplary embodiments, the values of the resistors are chosen such that the resultant gain achieved by the 8-switch DIP-switch advances the base gain in increments corresponding to the binary status of the switches. For example, if only the first and the eighth switch of the DIP-switch are turned on, the circuit will provide the amplifier with a gain having a relative value equal to the base gain plus 129. Since the DIP-switch has 8 switches, the circuit can produce gain values having 256 gradations.

The threshold value selected by the threshold circuitry 80 can be chosen in a similar manner, as illustrated in FIG. 10. As illustrated, a 4-switch DIP-switch 110 allows the operator to select between four different threshold values—30%, 40%, 50% and 60%. Unlike the amplifier 76, however, the DIP-switch 110 is not binary encoded. One switch should be on at one time, which selects one of the resistors R12–R15. These resistors supplement the resistance provided by resistors R16 and R17, and thus, in conjunction with signal divider 112, provide the desired threshold level signal for input to the comparator circuit 82.

The comparator circuit 82 compares the threshold signal with the output of the AC amplifier 76 to produce an indication of whether or not a band is present. The comparator circuit can include conventional comparator components, such as resistors R18 and R19, capacitors C3 and C4 and comparator 114, as will be readily understood by those skilled in the art. Similarly, the remainder of the circuit blocks shown in FIG. 8 can comprise conventional circuitry and thus, so as not to obfuscate the discussion, will not be discussed further herein.

The output of the comparator 82 is sent to the interface 216 and then to computer 218 (with reference to FIG. 3). According to exemplary embodiments of the present invention, the computer samples the data from the sensor every 0.25 mm. As mentioned, the computer can be used to transmit reject signals to the cigarette making machine 200. Furthermore, the computer can present statistical displays of the integrity of bands detected by the sensor.

In operation, the computer 218 is used to analyze the band signal output from the sensor, in conjunction with the encoder signal, to provide an indication of whether the band widths and spacings are out-of-tolerance. To this end, the computer stores a batch file containing values input by the operator indicating a minimum band width, maximum bandwidth, minimum band spacing, and maximum band spacing. The signal from the sensor is compared with reference to these tolerance values. The computer maintains a log of out-of-tolerance band widths and spacings for display to the user.

Also, as mentioned, the computer provides a signal to the cigarette making machine 200 to inform the machine to reject cigarettes which will be subsequently constructed from the portions of the cigarette paper containing irregular bands. More specifically, this signal will be transmitted to the cigarette making machine when the band widths are too long or too short, or when the band spacing is too long or too short. As an additional safeguard, if the distance between regular bands exceeds 20 maximum band spacings, the missing band detector can be configured to transmit rejection signals to the cigarette making machine until it finds 10 properly spaced bands. The computer 218 can also transmit cigarette reject signals to the cigarette making machine when the sensor generates an alarm condition. However, in all of the above circumstances, the computer can be precluded from transmitting any signals to the cigarette making machine if the encoder indicates that the machine is operating at speeds outside (e.g. below) a prescribed value.

Figure 11A:
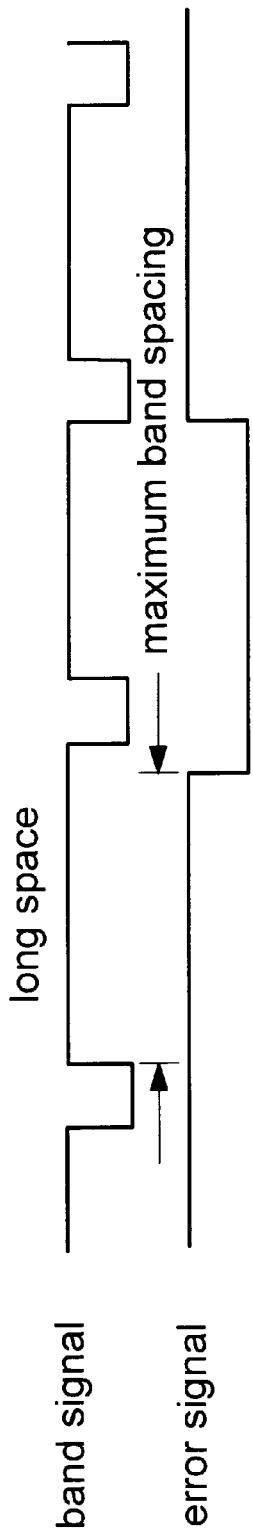
FIGS. 11(a)–11(g) show exemplary comparisons of the output of the band sensor with various user-specified tolerance values according to the present invention.
Figure 11B:
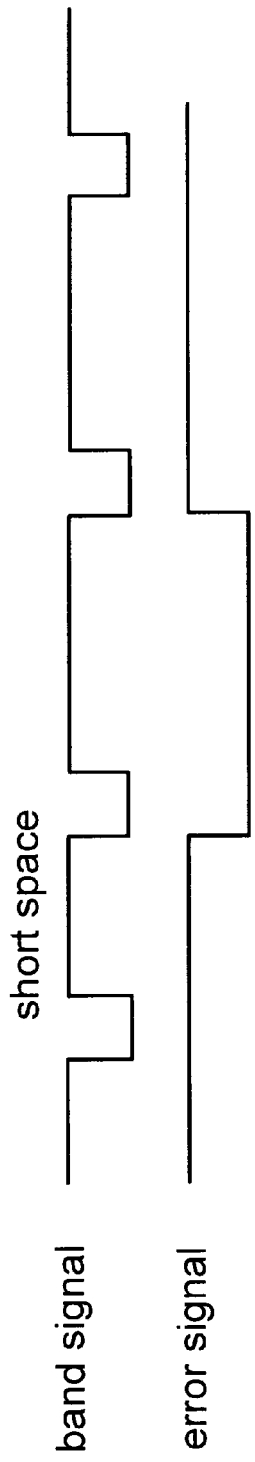

The operation of the algorithm which the computer 218 used to assess the integrity of bands on the cigarette paper can be more readily understood with reference to FIGS. 11(a) to 11(g). FIG. 11(a) illustrates the situation where the output of the sensor in its band-following mode exceeds the maximum band spacing input by the operator, upon which the computer asserts an anomaly signal. The anomaly signal is deactivated when a regular band spacing is measured, or after 5 ms, whichever is longer. FIG. 11(b) illustrates the opposite situation, where the output of the sensor reveals a band which is too short. The computer asserts an anomaly signal until the banding spacing becomes regular, or after 5 ms, whichever is longer.

Figure 11C:
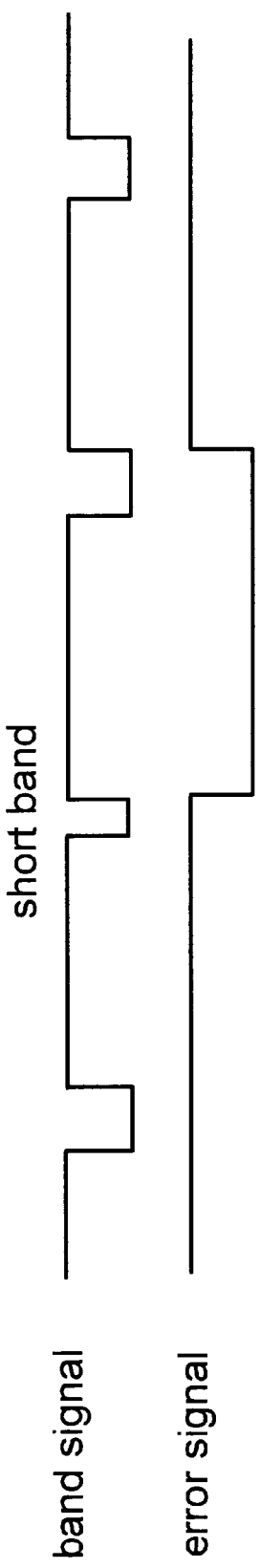
Figure 11D:
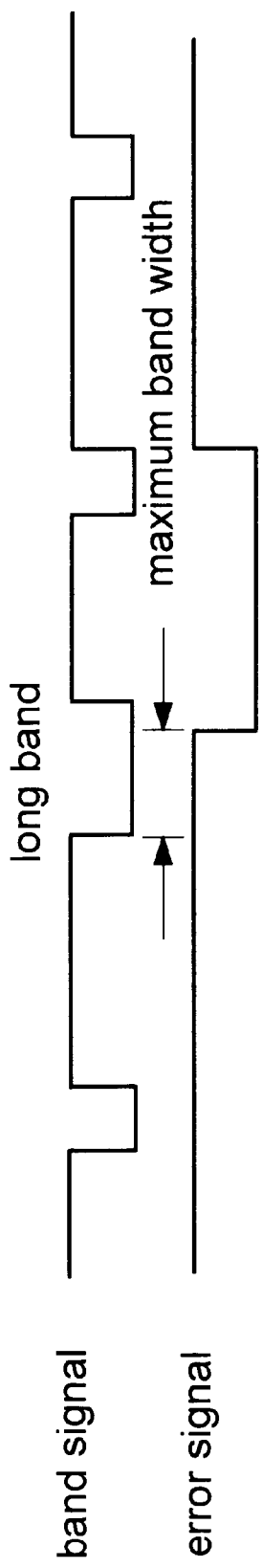

FIG. 11(c) shows the generation of an anomaly signal upon detecting the occurrence of a band which is too short. FIG. 11(d) shows the generation of an anomaly signal upon detecting the occurrence of band which is too long. In both cases the anomaly signal is deactivated when the band is measured having regular width or after 5 ms, whichever is longer.

Figure 11E:
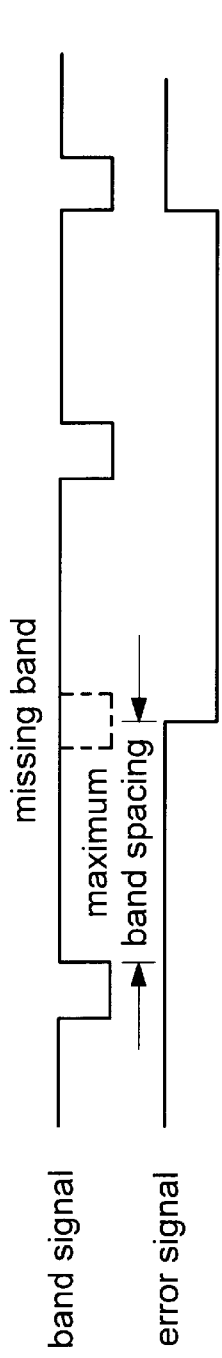
Figure 11F:
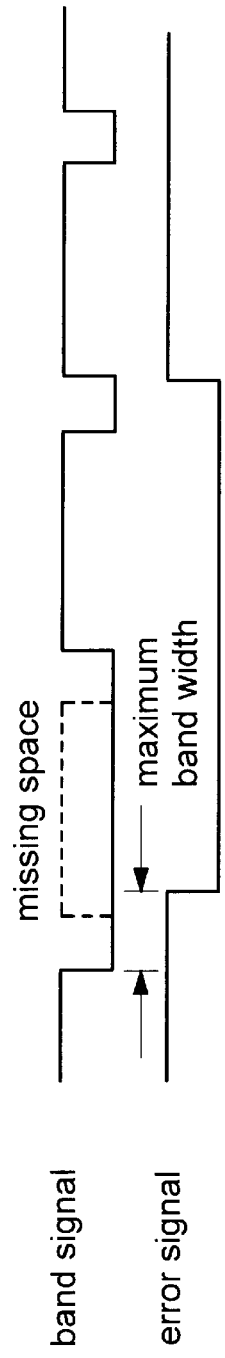

FIG. 11(e) shows the generation of an anomaly signal upon detecting a missing band. More specifically, the anomaly signal is asserted when the maximum spacing as specified by the operator is reached without the detection of a band. Similarly, FIG. 11(f) shows the generation of an anomaly signal in response to the detection of a missing space. The anomaly signal is asserted when the maximum band width as specified by the operator is reached without the detection of a space.

Figure 11G:
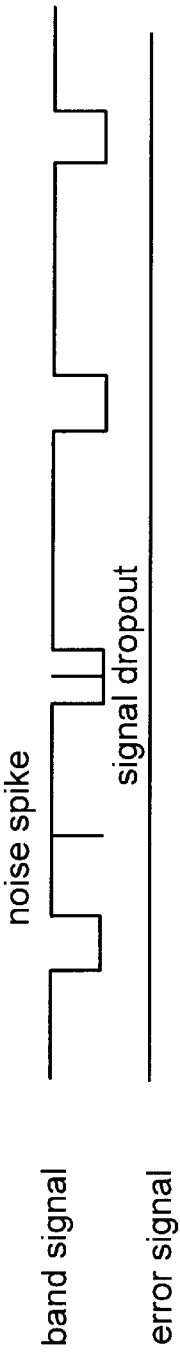

Finally, FIG. 11(g) shows that the algorithm can comprise software which filters and eliminates small perturbations in the output of the sensor. Accordingly, these small perturbations (such as noise spikes and signal dropouts) do not falsely signal the termination or the start of a band or space.

Statistics regarding a bobbin of cigarette paper are accumulated by the computer 218 and displayed to the operator. An exemplary display is shown in FIG. 12. The display shows the setup information from the batch file, containing the minimum band width (in mm), the maximum band width, the minimum band spacing and the maximum band spacing. The display presents the number of bands within limits, number of bands outside of limits, and the number of spaces outside of limits. The display presents the average and standard deviation of band width, as well as the minimum and maximum band width. The display presents the same information with respect to band spacing. For frame of reference, the display presents the paper speed as measured by the encoder, as well as whether an alarm condition is currently active. Depending on the choice of the operator, the system can be disabled from accumulating band statistics while the device is in an error mode.

All of the above identified information can be stored by the computer and later retrieved for analysis, or comparison with other runs.

The above-described exemplary embodiments are intended to be illustrative in all respects, rather than restrictive, of the present invention. Thus the present invention is capable of many variations in detailed implementation that can be derived from the description contained herein by a person skilled in the art. All such variations and modifications are considered to be within the scope and spirit of the present invention as defined by the following claims.

By way of example, the present invention has been described in the context of the optical inspection of cigarette paper containing bands. However, the principles of the invention apply to the inspection of other types of web material having various types of indices formed thereon. Furthermore, the sensor has been described in the environment of a cigarette making machine. However, the sensor has other uses. For instance, the sensor can be used to detect bands formed on cigarette paper as the paper is transferred from a first bobbin (unwind bobbin) to a second bobbin (rewind bobbin). Related patent application Ser. No. 08/893,500, which is incorporated here by reference, illustrates the use of the sensor in such a machine.

What is claimed is:

1. An optical system for inspecting a web of material containing bands, comprising:

an emitter for directing radiation onto said web of material containing bands, said radiation impinging on a surface of said web of material and creating reflections;

a detector for receiving said reflections and forming electrical signals representative of said reflections;

circuitry for processing said electrical signals by determining presence of bands on said web to generate Output signals; and computing logic for receiving said output signals and for determining if said reflections are representative of bands on said web of paper which are irregular;

wherein said circuitry for processing said electrical signals includes a peak detector for ascertaining a peak level signal of said electrical signals.

2. The cigarette making system of claim 1, where said detection logic detects that said output signals are indicative of irregular bands by determining whether said output signals are indicative of at least one of:

a band having an out-of-tolerance width; and at least two adjacent bands having out-of-tolerance spacing.

3. The optical system according to claim 1, wherein said circuitry for processing said electrical signals includes a threshold circuit for forming a threshold signal which is a percentage of said peak level signal.

4. The optical system according to claim 3, wherein said circuitry for processing said electrical signals includes comparator circuitry for comparing said threshold signal with said electrical signals, wherein electrical signals which exceed said threshold signal are indicative of regions of said web containing bands, and electrical signals which do not exceed said threshold signal are indicative of regions of said web not containing bands.

5. The optical system according to claim 3, wherein said percentage can be selected by an operator.

6. The optical system according to claim 1, wherein said computing logic assesses that at least one band is irregular by detecting that said output signals reveal that:

at least one of said bands is shorter than a prescribed value;

at least one of said bands is longer than a prescribed value;

a spacing between at least two adjacent bands is below a prescribed value; or a spacing between at least two adjacent bands is above a prescribed value.

7. The optical system according to claim 1, wherein said processing circuitry includes an amplifier for amplifying an AC component of said electrical signals.

8. The optical system according to claim 7, wherein said amplifier includes an adjustment element whereby an operator can adjust the value of a gain of the amplifier.

9. The optical system according to claim 1, further including output circuitry for informing a cigarette making machine to reject cigarettes when the computing logic detects irregular bands.

10. A method for optically inspecting a web containing bands, including the steps of:

illuminating a surface of said web with radiation, said radiation forming reflections;

sensing said reflections Using a detector, and forming electrical signals representative of said reflections;

processing said electrical signals to detect the presence of bands on said web to produce output signals; and analyzing said output signals to detect irregular bands;

wherein said processing step further includes the step of;

forming a peak value signal representative of peak values of said electrical signals.

11. The method of claim 10, wherein said processing step further includes the steps of:

forming a threshold signal representative of a percentage of said peak value signal; and comparing said threshold signal with said electrical signals to determine a presence of said bands on said web.

12. The method of claim 10, wherein said analyzing step further includes the steps of assessing whether:

at least one band is shorter than a prescribed value;

at least one band is longer than a prescribed value;

the spacing between at least two adjacent bands is below a prescribed value; or the spacing between at least two adjacent bands is above a prescribed value.

13. The method of claim 10, further including the step of presenting a display showing a statistical summary of irregular bands.

14. The method of claim 10, further including the step of informing a cigarette making machine of the presence of irregular bands, so that said cigarette making machine can reject cigarettes made from portions of said web containing said irregular bands.

* * * * *